United States Patent
Rogers et al.

(10) Patent No.: US 10,758,227 B2
(45) Date of Patent: Sep. 1, 2020

(54) DELIVERING BIOABSORBABLE FASTENERS

(71) Applicant: Opus KSD Inc., Peacham, VT (US)

(72) Inventors: Charles H. Rogers, Halifax, MA (US); Eduard U. Milea, Irvine, CA (US)

(73) Assignee: Opus KSD Inc., Pembroke, MA (US)

( * ) Notice: Subject to any disclaimer, the term of this patent is extended or adjusted under 35 U.S.C. 154(b) by 282 days.

(21) Appl. No.: 15/950,799

(22) Filed: Apr. 11, 2018

(65) Prior Publication Data

US 2018/0228488 A1    Aug. 16, 2018

Related U.S. Application Data

(63) Continuation of application No. 14/957,206, filed on Dec. 2, 2015, now Pat. No. 10,045,777, which is a continuation of application No. 13/755,540, filed on Jan. 31, 2013, now Pat. No. 9,232,943.

(51) Int. Cl.
*A61B 17/068* (2006.01)
*A61B 17/04* (2006.01)
*A61B 17/072* (2006.01)

(52) U.S. Cl.
CPC ........ *A61B 17/068* (2013.01); *A61B 17/0401* (2013.01); *A61B 17/0682* (2013.01); *A61B 2017/0409* (2013.01); *A61B 2017/0412* (2013.01); *A61B 2017/0416* (2013.01); *A61B 2017/0419* (2013.01); *A61B 2017/0427* (2013.01); *A61B 2017/0445* (2013.01); *A61B 2017/0464* (2013.01); *A61B 2017/07271* (2013.01)

(58) Field of Classification Search
CPC . A61B 17/068; A61B 17/0401; A61B 17/062; A61B 2017/0409; A61B 2017/0412; A61B 2017/0416; A61B 2017/0427; A61B 2017/0464; A61B 2017/07271
USPC ........................................ 227/175.1
See application file for complete search history.

(56) References Cited

U.S. PATENT DOCUMENTS

| | | | |
|---|---|---|---|
| 2,206,460 | A | 7/1940 | Hansen |
| 2,457,362 | A | 12/1948 | Giglio |
| 3,716,058 | A | 2/1973 | Tanner, Jr. |
| 3,875,648 | A | 4/1975 | Bone |

(Continued)

FOREIGN PATENT DOCUMENTS

| | | | |
|---|---|---|---|
| EP | 0589306 | A2 | 3/1994 |
| EP | 1531736 | A2 | 5/2005 |

(Continued)

OTHER PUBLICATIONS

Non-Final Office Action dated Apr. 19, 2018 for U.S. Appl. No. 14/925,355 (34 Pages).

(Continued)

*Primary Examiner* — Michelle Lopez
(74) *Attorney, Agent, or Firm* — Brown Rudnick LLP

(57) ABSTRACT

An apparatus includes a housing, an actuator, and a plurality of fasteners. The apparatus is for closing two sides of an incision or cut in skin tissue. The actuator moves into and out of the housing. The plurality of the fasteners are within the housing, and the apparatus is operable to deliver one fastener at a time into each of the two sides of the incision or cut.

16 Claims, 7 Drawing Sheets

(56) References Cited

U.S. PATENT DOCUMENTS

| | | | |
|---|---|---|---|
| 4,179,063 A | 12/1979 | Russell | |
| 4,410,125 A | 10/1983 | Noiles et al. | |
| 4,627,437 A | 12/1986 | Bedi et al. | |
| 4,669,473 A | 6/1987 | Richards et al. | |
| 4,736,746 A | 4/1988 | Anderson | |
| 4,867,083 A | 9/1989 | Fietta et al. | |
| 4,994,073 A | 2/1991 | Green | |
| 5,089,009 A | 2/1992 | Green | |
| 5,269,783 A | 12/1993 | Sander | |
| 5,342,376 A | 8/1994 | Ruff | |
| RE34,891 E | 4/1995 | Kunreuther | |
| 5,466,243 A | 11/1995 | Schmieding et al. | |
| 5,489,287 A | 2/1996 | Green et al. | |
| 5,515,797 A | 5/1996 | Janouschek et al. | |
| 5,584,859 A | 12/1996 | Brotz | |
| 5,615,816 A | 4/1997 | Deschenes et al. | |
| 5,618,311 A | 4/1997 | Gryskiewicz | |
| 5,641,234 A | 6/1997 | Blumberg | |
| 5,643,319 A | 7/1997 | Green et al. | |
| 5,718,359 A | 2/1998 | Palmer et al. | |
| 5,755,371 A | 5/1998 | Huang | |
| 5,810,851 A | 9/1998 | Yoon | |
| 5,891,168 A | 4/1999 | Thal | |
| 5,984,949 A | 11/1999 | Levin | |
| 6,179,840 B1 | 1/2001 | Bowman | |
| 6,190,401 B1 | 2/2001 | Green et al. | |
| 6,200,330 B1 | 3/2001 | Benderev et al. | |
| 6,325,007 B1 | 12/2001 | Farmer | |
| 6,387,113 B1 | 5/2002 | Hawkins et al. | |
| 6,423,073 B2 | 7/2002 | Bowman | |
| 6,485,504 B1 | 11/2002 | Johnson et al. | |
| 6,551,343 B1 | 4/2003 | Tormala et al. | |
| 6,554,852 B1 | 4/2003 | Oberlander | |
| 6,601,748 B1 | 8/2003 | Fung et al. | |
| 6,610,079 B1 | 8/2003 | Li et al. | |
| 6,652,563 B2 | 11/2003 | Dreyfuss | |
| 6,663,633 B1 | 12/2003 | Pierson, III | |
| 6,726,705 B2 | 4/2004 | Peterson et al. | |
| 6,733,506 B1 | 5/2004 | McDevitt et al. | |
| 6,830,573 B2 | 12/2004 | Strong et al. | |
| 6,991,643 B2 | 1/2006 | Saadat | |
| 7,004,950 B1 | 2/2006 | Collins et al. | |
| 7,028,878 B2 | 4/2006 | Bauer | |
| 7,033,379 B2 | 4/2006 | Peterson | |
| 7,048,171 B2 | 5/2006 | Thornton et al. | |
| 7,056,331 B2 | 6/2006 | Kaplan et al. | |
| 7,104,999 B2 | 9/2006 | Overaker | |
| 7,112,214 B2 | 9/2006 | Peterson et al. | |
| 7,118,581 B2 | 10/2006 | Friden | |
| D532,107 S | 11/2006 | Peterson et al. | |
| 7,413,570 B2 | 8/2008 | Zamierowski | |
| 7,547,315 B2 | 6/2009 | Peterson et al. | |
| 7,682,372 B2 | 3/2010 | Peterson | |
| 7,686,200 B2 | 3/2010 | Peterson | |
| D635,259 S | 3/2011 | Peterson et al. | |
| 7,950,559 B2 | 5/2011 | Peterson et al. | |
| 8,016,867 B2 | 9/2011 | Bowman | |
| 8,066,736 B2 | 11/2011 | Peterson et al. | |
| 8,074,857 B2 | 12/2011 | Peterson et al. | |
| 8,100,939 B2 | 1/2012 | Peterson | |
| 8,105,342 B2 | 1/2012 | Onuki et al. | |
| 8,506,591 B2 | 8/2013 | Danielson et al. | |
| 8,821,517 B2 | 9/2014 | Peterson et al. | |
| 8,821,939 B2 | 9/2014 | Ryan et al. | |
| 9,232,943 B2* | 1/2016 | Rogers | A61B 17/0401 |
| 9,713,472 B2 | 7/2017 | Peterson et al. | |
| 10,045,777 B2* | 8/2018 | Rogers | A61B 17/0682 |
| 2001/0027322 A1* | 10/2001 | Bowman | A61B 17/0401 606/104 |
| 2001/0039436 A1 | 11/2001 | Frazier et al. | |
| 2002/0111641 A1 | 8/2002 | Peterson et al. | |
| 2003/0167072 A1 | 9/2003 | Oberlander | |
| 2003/0208211 A1 | 11/2003 | Kortenbach | |
| 2003/0236550 A1 | 12/2003 | Peterson et al. | |
| 2004/0059377 A1 | 3/2004 | Peterson et al. | |
| 2005/0116008 A1 | 6/2005 | Thornton et al. | |
| 2005/0149064 A1 | 7/2005 | Peterson et al. | |
| 2005/0288689 A1 | 12/2005 | Kammerer et al. | |
| 2006/0009792 A1 | 1/2006 | Baker et al. | |
| 2006/0011693 A1 | 1/2006 | Wywialowski et al. | |
| 2006/0097027 A1 | 5/2006 | Brown | |
| 2006/0122635 A1 | 6/2006 | Naegeli et al. | |
| 2006/0135988 A1 | 6/2006 | Peterson | |
| 2006/0253131 A1 | 11/2006 | Wolniewicz | |
| 2008/0249563 A1 | 10/2008 | Peterson et al. | |
| 2009/0206127 A1* | 8/2009 | Danielson | A61B 17/064 227/175.1 |
| 2010/0292715 A1 | 11/2010 | Nering et al. | |
| 2012/0083831 A1 | 4/2012 | Peterson | |
| 2012/0145765 A1 | 6/2012 | Peterson et al. | |
| 2012/0325889 A1 | 12/2012 | Danielson et al. | |
| 2016/0242772 A1 | 8/2016 | Peterson et al. | |

FOREIGN PATENT DOCUMENTS

| | | |
|---|---|---|
| EP | 1545385 A2 | 6/2005 |
| JP | 2004-516211 A | 6/2004 |
| JP | 2004-516263 A | 6/2004 |
| JP | 2005-530563 A | 10/2005 |
| JP | 2005-530567 A | 10/2005 |
| JP | 4437317 B2 | 3/2010 |
| JP | 4786902 B2 | 10/2011 |
| WO | 8505025 A1 | 11/1985 |
| WO | 03071962 A2 | 9/2003 |
| WO | 2004/000104 A2 | 12/2003 |
| WO | 2004/000105 A2 | 12/2003 |
| WO | 2008005465 A2 | 1/2008 |
| WO | 2010141872 A1 | 12/2010 |

OTHER PUBLICATIONS

Advertising Document, Exhibit 1020, Inter Partes Review of U.S. Pat. No. 8,821,517, AIA Review No. IPR2017-01468, dated Sep. 18, 2017 (2 pages).

Conduct of the Proceeding, Paper #7, Inter Partes Review of U.S. Pat. No. 8,821,517, AIA Review No. IPR2017-01468, dated Sep. Aug. 30, 2017 (5 pages).

Corrected Reply on Motion to Deem Statements of Material Facts Admitted, Paper #13, Inter Partes Review of U.S. Pat. No. 8,821,517, AIA Review No. IPR2017-01468, dated Sep. 19, 2017 (11 pages).

Danielson, Kenneth S., et al., Assessment of a Novel Subcutaneous, Bioabsorbable Skin Closure System, Presented Apr. 20, 2013 Emerging Technology Session, SAGES 2013 annual meeting, Baltimore, MD [retrieved on Oct. 23, 2013]. Retrieved from the Internet: <URL: http://media.wix.com/ugd/f91d84_9056cb0c70e64ac2f1202949444921bc.pdf>.

Declaration of Charles H. (Chuck) Rogers, Exhibit 1002, Inter Partes Review of U.S. Pat. No. 8,821,517, AIA Review No. IPR2017-01468, dated May 15, 2017 (22 pages).

Declaration of Peter Stokes, Exhibit 1012, Inter Partes Review of U.S. Pat. No. 8,821,517, AIA Review No. IPR2017-01468, May 9, 2017 (60 pages).

Declration of H.V. Mendenhall, Exhibit 1017, Inter Partes Review of U.S. Pat. No. 8,821,517, AIA Review No. IPR2017-01468, dated May 15, 2017 (18 pages).

Ethicon Wound Closure Manual Excerpts, Exhibit 1015, Inter Partes Review of U.S. Pat. No. 8,821,517, AIA Review No. IPR2017-01468, dated May 15, 2017 (11X pages).

Examination Report dated Mar. 24, 2017 for Indian Patent Application No. 5191/KOLNP/2008 (9 Pages).

Extended European Search Report for Application No. 07810174.8, dated Dec. 21, 2012, 8 pages.

Extended European Search Report for Application No. 13194162.7, dated May 8, 2014, 7 pages.

Extended European Search Report for Application No. 15167751.5, dated Jan. 20, 2016, 9 pages.

International Preliminary Report on Patentabiilty for corresponding international application No. PCT/US07/15418, dated Jan. 6, 2009, 4 pages.

(56) References Cited

OTHER PUBLICATIONS

International Search Report for corresponding international application No. PCT/US07/15418, dated Sep. 8, 2008, 6 pages.
Motion to Deem Material Facts Admitted, Paper #8, Inter Partes Review of U.S. Pat. No. 8,821,517, AIA Review No. IPR2017-01468, dated Sep. 5, 2017 (11 pages).
Patent Owner Letter, Exhibit 1009, Inter Partes Review of U.S. Pat. No. 8,821,517, AIA Review No. IPR2017-01468, dated May 15, 2017 (2 pages).
Patent Owner Opposition to Petitioner Motion, Paper #11, Inter Partes Review of U.S. Pat. No. 8,821,517, AIA Review No. IPR2017-01468, dated Sep. 12, 2017 (14 pages).
Patent Owner Preliminary Response, Paper #6, Inter Partes Review of U.S. Pat. No. 8,821,517, AIA Review No. IPR2017-01468, dated Aug. 18, 2017 (19 pages).
Patent Owner Sur-Reply to Petitioner Reply to Preliminary Response, Paper #10, Inter Partes Review of U.S. Pat. No. 8,821,517, AIA Review No. IPR2017-01468, dated Sep. 12, 2017 (14 pages).
Pediatric Emergency Procedures, Exhibit 1014, Inter Partes Review of U.S. Pat. No. 8,821,517, AIA Review No. IPR2017-01468, dated May 15, 2017 (7 pages).
Petition for Inter Partes Review of U.S. Pat. No. 8,821,517, AIA Review No. IPR2017-01468, May 15, 2017 (80 pages).
Petitioner Reply to Motion to Deem Statements of Material Facts Admitted, Paper #12, Inter Partes Review of U.S. Pat. No. 8,821,517, AIA Review No. IPR2017-01468, dated Sep. 18, 2017 (13 pages).
Photograph, Exhibit 1010, Inter Partes Review of U.S. Pat. No. 8,821,517, AIA Review No. IPR2017-01468, dated May 15, 2017 (2 pages).
Photograph, Exhibit 1011, Inter Partes Review of U.S. Pat. No. 8,821,517, AIA Review No. IPR2017-01468, dated May 15, 2017 (2 pages).
Photographs, Exhibits 1007A and 1007B, Inter Partes Review of U.S. Pat. No. 8,821,517, AIA Review No. IPR2017-01468, dated May 15, 2017 (4 pages).
Principles of Wound Management, Exhibit 1013, Inter Partes Review of U.S. Pat. No. 8,821,517, AIA Review No. IPR2017-01468, dated May 15, 2017 (9 pages).
Reply to Preliminary Response, Paper #9, Inter Partes Review of U.S. Pat. No. 8,821,517, AIA Review No. IPR2017-01468, dated Sep. 5, 2017 (11 pages).
SubQ It!™ Bioabsorbable Skin Stapler 90 Day Animal Study. Opus KSD, Inc., 2013 [retrieved on Oct. 23, 2013]. Retrieved from the Internet: <URL: http://www.subq-it.com/#!studies/cfvg <http://www.subq-it.com/>.
Trial Instituted Document, Paper #14, Inter Partes Review of U.S. Pat. No. 8,821,517, AIA Review No. IPR2017-01468, dated Nov. 15, 2017 (9 pages).
Written Opinion of the International Searching Authority for corresponding international application No. PCT/US07/15418, dated Jan. 1, 2009, 3 pages.

* cited by examiner

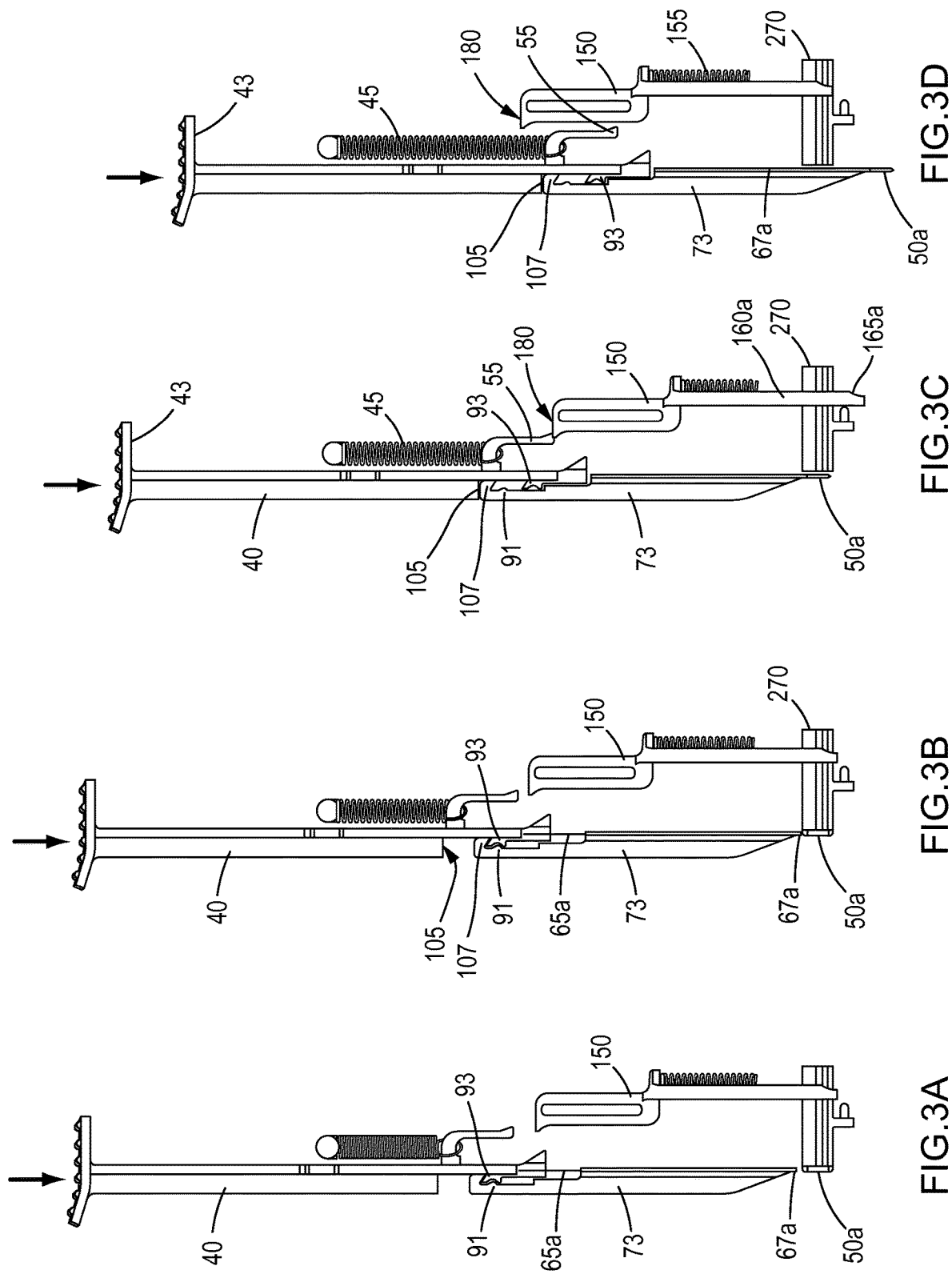

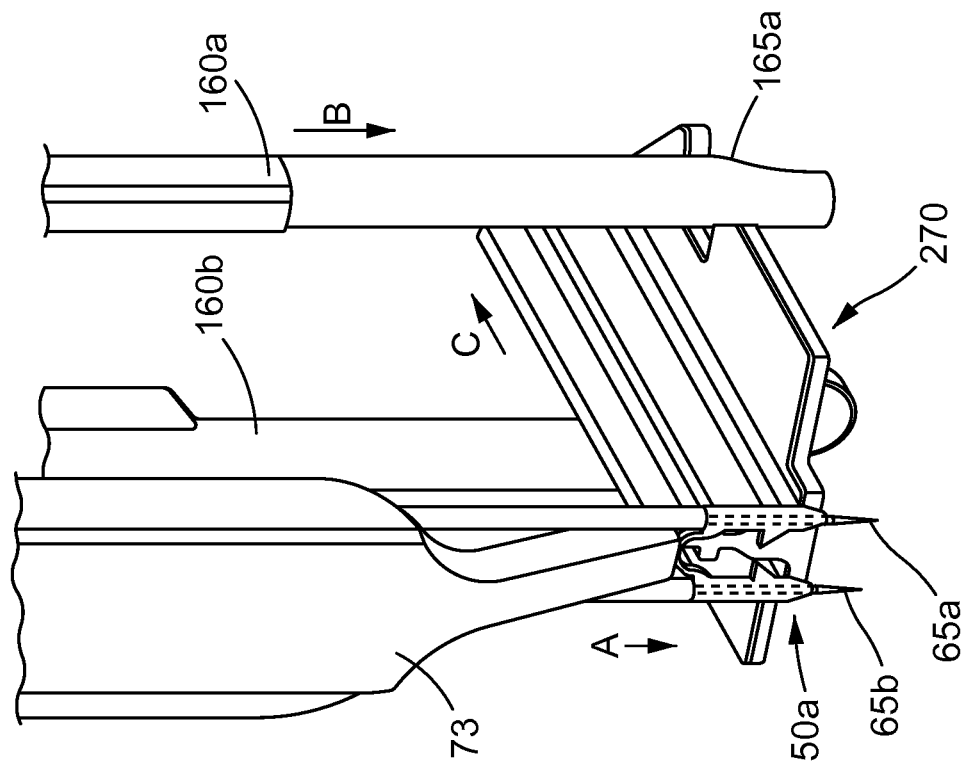
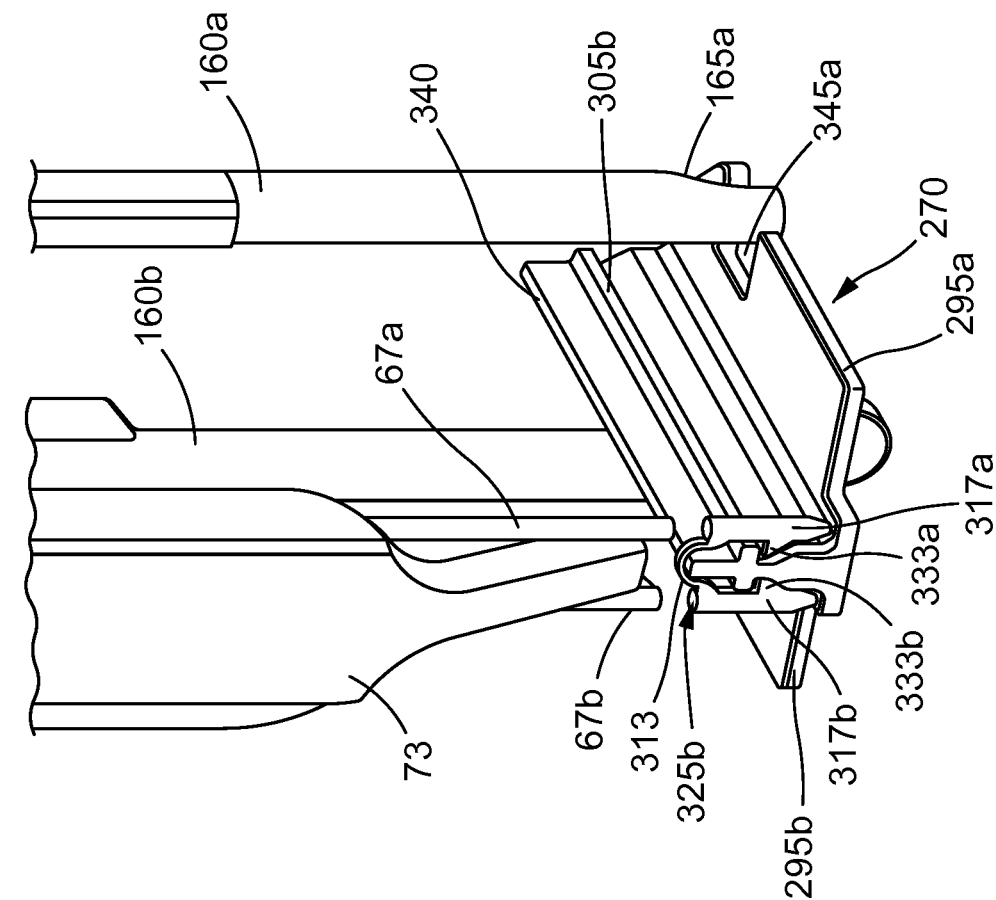
FIG.6A
FIG.6B

DELIVERING BIOABSORBABLE FASTENERS

PRIORITY INFORMATION

This application is a continuation of U.S. patent application Ser. No. 14/957,206 filed Dec. 2, 2015, which is a continuation of U.S. patent application Ser. No. 13/755,540 filed Jan. 31, 2013 (now U.S. Pat. No. 9,232,943), the contents of each of which are incorporated herein by reference in their entirety.

FIELD OF THE INVENTION

The invention relates to sequentially deploying a plurality of bioabsorbable fasteners into tissue to secure two sides of an incision or cut in the skin or other tissue of a patient.

BACKGROUND OF THE INVENTION

There are many examples of surgical staplers which deliver staples one at a time. Most of these deliver traditional metal staples which rely on the strength of the staple to pierce the tissue and to hold the tissue surfaces together. Hence the typical surgical stapler engages the first staple at the front of a linear array of staples, and pushes it into the tissue while bending it over an anvil. Once the staple is bent into position, the tissue surfaces that are being held cannot un-bend the metal staple. One of the disadvantages of the metal staple is that it must have a portion that remains exposed through the skin surface in order to allow a medical professional to remove the fastener once biological healing is complete. This exposed portion is unsightly, and the puncture points where the fastener enters the skin, have a risk of infection.

To address the disadvantages of metal staples, various inventors have proposed fasteners made of bioabsorbable materials which can be placed below the surface of the skin. This subcuticular skin closure avoids punctures through the epidermis, and does not require follow-up removal of the staples. Such a fastener is described in U.S. Pat. No. 6,726,705 to Peterson et al, as a "Mechanical Method and Apparatus for Bilateral Tissue Fastening". A product based on this patent, the INSORB® Subcuticular Skin Stapler, has been commercialized by Incisive Surgical of Plymouth, Minn. The fastener deployed by the INSORB device is significantly thicker in cross section than a metal staple to enable the plastic material to be strong enough to maintain the traditional "U" shape of a staple during the healing process. This added bulk is undesirable as it takes longer to be absorbed by the body. Also the head of the INSORB stapler must be inserted within the incision to deploy the fastener. This means that the user has poor visibility as to the placement of the fastener and that the device cannot be used on small incisions such as those employed in increasingly popular minimally invasive surgery.

SUMMARY OF THE INVENTION

An objective of the present invention is to provide a stapler apparatus, that is easily operated by a user, to aid in the insertion of one or more bioabsorbable fasteners for closing incisions, including small incisions such as ones that are less than 10 mm long. Another objective of the present invention is to provide good visibility to the operator of the site where the fastener will be inserted. Yet another objective is to provide a stapler loadable, or preloaded, with multiple fasteners stored in a magazine or cartridge, where the stapler is able to deploy the fasteners one at a time. A sufficient number of fasteners can be loaded or preloaded, or different configurations of the stapler can be provided, to close long as well as short incisions. Another objective of the present invention is to provide a locking mechanism that prevents fasteners from being accidentally discharged during shipment or handling prior to intentional use. An additional objective is to provide a stapler with a safety mechanism that prevents the needles from being exposed after the last fastener is delivered by the stapler.

The present application and invention is directed to a surgical stapling apparatus able to deploy fasteners of the type described by Danielson et. al. in US patent application publication number 2009/0206127 A1 "Tissue Fasteners and Related Insertion Devices, Mechanisms, and Methods" (hereinafter "Danielson"), which is incorporated herein by reference in its entirety. The present invention relates to a new and innovative delivery device that is not disclosed in Danielson and that can be used by an operator (such as a surgeon or other medical professional) to insert into tissue of a patient (such as a human or other mammal) the bioabsorbable fasteners disclosed in Danielson and to insert them generally in accordance with the insertion procedure/steps set forth in Danielson. Other types of bioabsorbable fasteners may also be used with and deployed by the disclosed apparatus.

The present invention relates to a mechanical apparatus for inserting needles into cannulated legs of a bioabsorbable fastener. The apparatus comprises a housing which orients and constrains other elements of the apparatus. Extending from the proximal end of the housing is an actuator that may be operated by the thumb of the user such that pressing the actuator into the housing causes a fastener, carried on needles and pushed by components operably connected to the actuator, to be deployed from the distal end of the housing. The housing further contains a magazine with a plurality of fasteners positioned on a reciprocally movable fastener support and a timing lever, which acts on the fastener support to move it and release each fastener one-by-one after the needles are inserted into the cannulated legs.

As the user continues to push the actuator, the needles and fastener exit the distal end of the housing and deliver the fastener between the two sides of a bifurcated foot over which the two sides of a patient's incision or cut have been positioned. The user has complete visibility of the fastener as it exits the housing before it enters the tissue, and thus can adjust the position of the stapler or tissue to precisely direct the fastener to the desired target. With manual control of speed and force, the user can deploy the fastener into the tissue such that the two legs of the fastener are inserted into the two sides of the incision. Upon releasing the actuator, it is returned by a spring to its starting position, thereby retracting the needles and leaving the fastener deployed beneath the surface of the tissue.

In order to reliably guide the needles into the cannulated legs of each fastener, the apparatus further comprises needle guide tubes made of cylindrical tubes which have an outside diameter similar in size to the outside diameter of the legs of the fastener. The distal ends of these needle guide tubes are slideably held by shaped features at the front of the magazine ("huggers") which simultaneously contact and align the needle guide tubes and the legs of the fastener as the needles exit the needle guide tubes and enter the fastener legs. The huggers reduce the impact of normal manufacturing and assembly imperfections and tolerances, and allow the critical step of inserting the needles into the cannulated legs of the fasteners to be achieved reliably, and repeatedly, for each and every fastener loaded (or preloaded) into the apparatus.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIGS. 3A through 3D show the sequence of positions of selected parts of the apparatus at different steps during the deployment of a fastener;

FIG. 6A shows a perspective view of the fastener support with the front-most fastener and guide tube support with needle guide tubes and timing lever positioned at the start of delivery of a fastener;

FIG. 6B shows the same perspective as FIG. 6A with the components positioned at an intermediate point in the delivery of the front-most fastener.

DETAILED DESCRIPTION

Figure 1A:
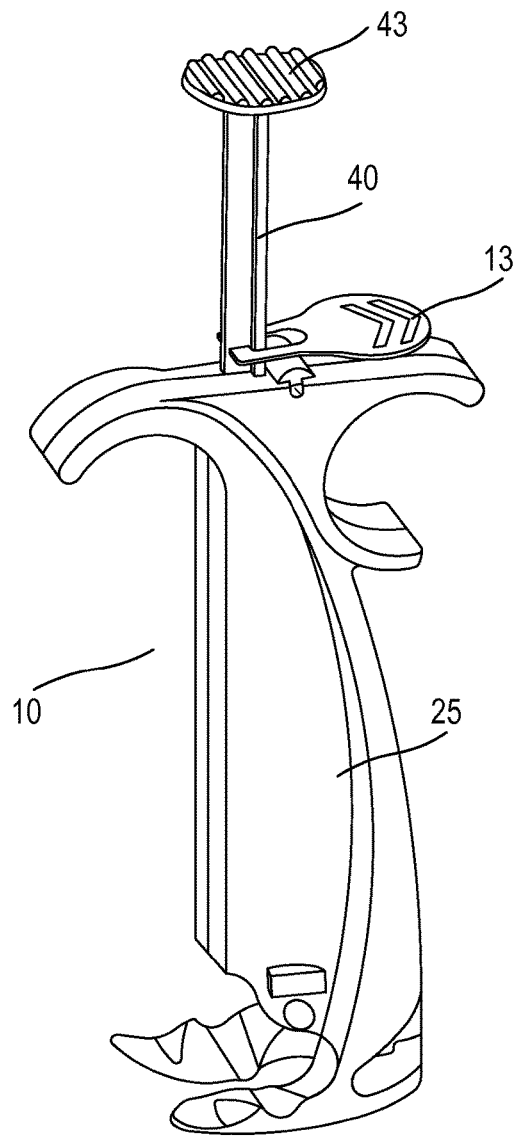
FIG. 1A shows a perspective view of the assembled apparatus of the present invention with safety lock installed.

FIG. 1A illustrates a perspective view of an apparatus 10 for inserting bioabsorbable fasteners to secure the two sides of an incision in tissue as illustrated in FIG. 1 and FIG. 2 of Danielson (US patent application publication number 2009/0206127 A1). For purposes of this description the proximal end, the end closest to the operator, is at the top of the figure and the distal end, the direction away from the operator, is at the bottom of the figure. FIG. 1A shows the apparatus as it may be presented to the user, preloaded with fasteners and secured with actuator lock 13, which serves as a safety to prevent the fasteners from being accidentally discharged during shipment or handling prior to their intentional use. Actuator lock 13 may be fabricated from a flexible plastic such as polypropylene by molding or die-cutting, for example, from sheet material approximately 0.030" thick.

Figure 1B:
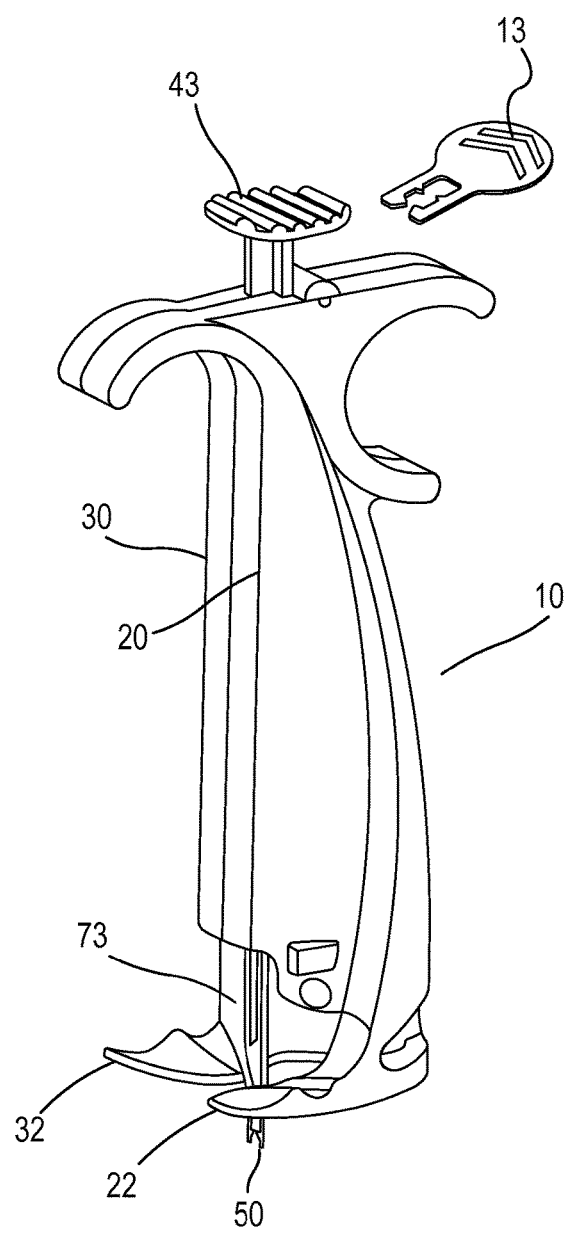
FIG. 1B shows the apparatus of the present invention with safety lock removed and actuator depressed fully to deliver a fastener.

Now with reference to FIGS. 1A and 1B, the apparatus 10 comprises a left housing shell 20 and a right housing shell 30 which are assembled together to form a housing 25 which orients and constrains other elements of the apparatus. Extending from the proximal end of the housing 25 is an actuator 40 that may be operated by the thumb of the user. As illustrated in FIG. 1B, removing the actuator lock 13 and pressing the actuator thumb pad 43, causes actuator 40 to move into the housing 25. Guiding surfaces and components described below operate within the housing 25 such that a fastener 50 is delivered through the opening in the distal end of the housing 25. The fastener is carried on needles, and guided by guide tube support 73, to move along a line centered between the left foot 22 and right foot 32, over which the two sides of the tissue (see FIG. 12a of Danielson) have been positioned. As illustrated in FIG. 12b of Danielson, the two legs of fastener 50 penetrate the two sides of the cut tissue (see 68a and 68b of Danielson). After inserting the fastener 50 into the tissue, the user releases pressure on actuator thumb pad 43, and a spring returns actuator 40 to the starting position. As the needles retract, the fastener 50 remains in the tissue as illustrated in FIG. 12c of Danielson. Finally as illustrated in FIG. 12d of Danielson, the barbs of the fastener engage, and the cut surfaces (68a and 68b of Danielson) return in anatomical apposition with one another.

Figure 2A:
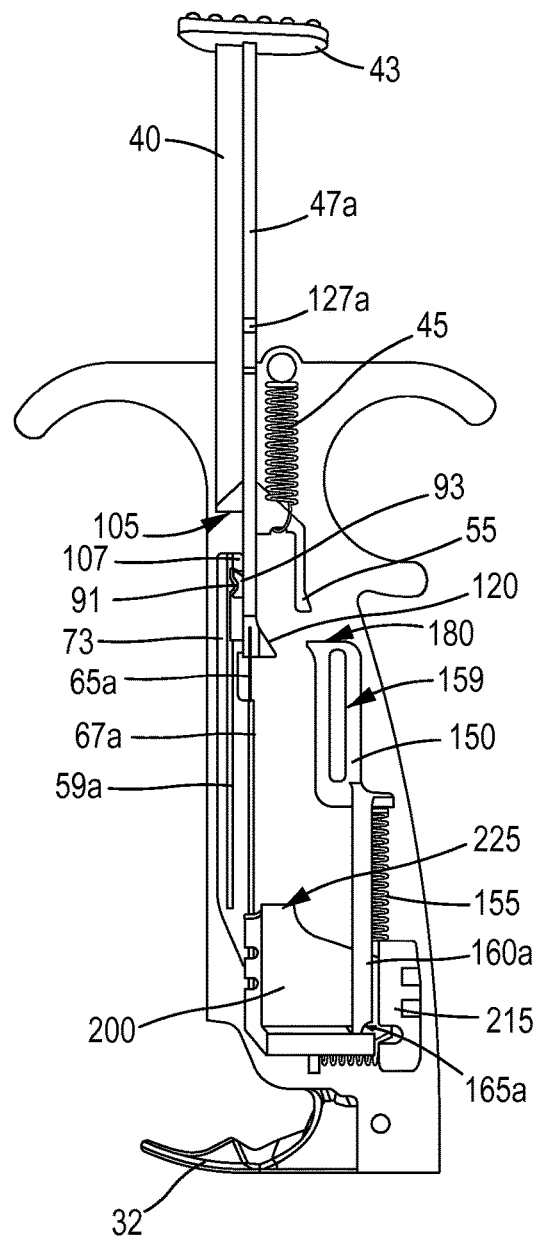
FIG. 2A shows components of the present invention with the left housing shell 20 removed to illustrate the components inside.
Figure 2B:
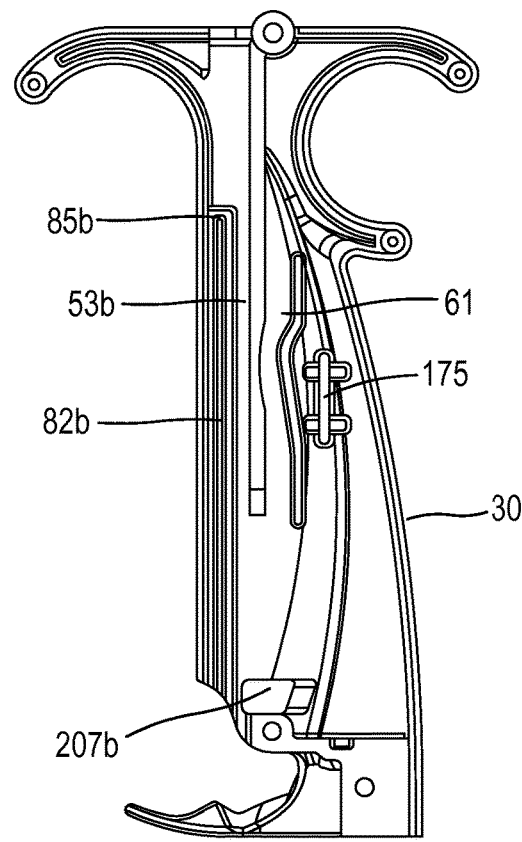
FIG. 2B shows the right housing shell of FIG. 2A with all components removed.

Now the various components of the apparatus 10 will be identified with reference to FIGS. 2A and 2B. FIG. 2A shows the components of the present invention with the left housing shell 20 removed to illustrate the components inside. FIG. 2B shows the right housing shell 30 alone, so that features that are obscured by the components in FIG. 2A, can be identified more easily. When components are symmetrical, the numbered features will be labeled with "a" for the left side and "b" for the right side, but in the text these symmetrical elements will be identified as "a,b", even if only one component is visible in a particular drawing.

Now turning to FIG. 2A, the actuator 40 is shown in the "up" or starting position, which is maintained by actuator return spring 45. The travel of actuator 40 is guided by actuator tongues 47a,b, which slide in actuator grooves 53a,b (see FIG. 2B). A resilient arm extending from the actuator 40, forms trigger 55, which is constrained to move in cam track 61 (see FIG. 2B). At the distal end of the actuator 40 needles 65a,b are rigidly fixed in place. The needles 65a,b are, in one embodiment of the apparatus 10, made from surgical grade stainless steel and secured to actuator 40 by adhesive bonding or by being over-molded with actuator 40 by injection molding practices known in the art.

Needles 65a,b are long and extend distally through the entire length of needle guide tubes 67a,b. The needle guide tubes 67a,b are rigidly attached to guide tube support 73. The travel of the guide tube support 73 is guided by guide tongues 59a,b which slide in guide grooves 82a,b (see FIG. 2B). The upward motion of the guide tube support 73 is limited by guide stops 85a,b (see FIG. 2B), which block the travel by interfering with the proximal end of guide tongues 59a,b.

The actuator 40 is able to push and pull the guide tube support 73, but does so indirectly by making contact with different surfaces at different times, as will be described below. A frictional engagement is provided by detent-protrusion 91 on guide tube support 73, which contacts a detent-receiver 93 on actuator 40. As the user continues to press on actuator thumb pad 43, the actuator moves and contact surface 105 on the actuator comes into contact with push-pull tab 107 on the guide tube support 73. This allows force to be transferred to needle guide tubes 67a,b to push the fastener into the tissue, as will be explained with reference to FIGS. 3A-3D. Actuator 40 also has an actuator stop protrusion 120, which extends outward from the axis of the actuator in order to contact the stop surface 225 on the top of the magazine 200. This interference limits the distal motion of the actuator 40, and hence the depth that the fastener is inserted into the tissue. After the fastener has been deployed, the actuator 40 is able to pull guide-tube support 73 when the proximal end of detent receiver 93 engages the push-pull tab 107, the position illustrated in FIG. 2A. Finally actuator 40 has lock receiver notches 127a,b, which allow actuator lock 13 (see FIG. 1A) to be inserted. When actuator lock 13 is inserted into actuator notches 127a,b, downward motion of actuator 40 is blocked.

Continuing with reference to FIG. 2A, a timing lever 150 is shown in the "up" or starting position, which is maintained by timing lever spring 155. The timing lever 150 has a proximal portion which includes timing lever slot 159 which slidably contacts timing lever tab 175 on right housing shell 30 (see FIG. 2B) to guide and limit the travel of the timing lever 150. Also, at the proximal end of timing lever 150, there is a trigger engagement surface 180, which is the proximal facing surface of a feature that protrudes from the part in order to provide momentary contact with trigger 55 on the actuator 40. The distal portion of timing lever 150 is split into two legs 160a and 160b. The distal ends of legs 160a,b have retractor contours 165a,b respectively, which will be described in more detail with the description of the timing sequence of FIGS. 3A-3D.

Finally shown in FIG. 2A is a magazine cap 215, which assembles together with magazine 200, to form an enclosure that contains a plurality of fasteners and other components that will be described with reference to FIG. 5. In an exemplary embodiment, magazine 200 and cap 215 are fabricated by injection molding processes from a plastic material such as Nylon 66 (for example natural Zytel® 103 available from E.I. DuPont de Nemours & Co. of Wilmington, Del.). The magazine 200 is loosely held in position within housing 25 by magazine tabs 205a,b (see FIG. 4), which extend through magazine slots 207a,b (see FIG. 2B).

The present invention will be better understood from a description of the different actions involved in deploying a fastener. The different steps are illustrated in FIGS. 3A-3D but the description will rely also on references to FIGS. 2, 5, 6A, and 6B. In FIG. 3A, the guide tube support 73, the actuator 40, and the timing lever 150 are all in their most proximal (up) position. At this, the starting point, the needles 65a,b are retracted such that their distal ends do not extend beyond the distal ends of the needle guide tubes 67a,b. This position, as illustrated in FIG. 2A, places distal ends of needles 65a,b 1 mm to 2 mm above the top of the front-most fastener 50a. When the user first pushes the actuator 40, the frictional engagement of detent-protrusion 91 on guide tube support 73 with detent-receiver 93 on actuator 40 causes the guide tube support 73 to move downward together with the actuator 40.

FIG. 3B illustrates the position of the same components as shown in FIG. 3A after the actuator 40 and guide tube support 73 have moved 1 mm to 2 mm, and the distal ends of the needle guide tubes 67a,b have made contact with the top of the front-most fastener 50a. At this point the fastener is still supported by the fastener support 270, and cannot move downward. This interference causes the detent-protrusion 91 to disengage from the detent-receiver 93, so that the actuator 40 can continue moving downward, while the needle guide tubes 67a,b temporarily remain motionless. An additional 1 mm to 2 mm of movement of actuator 40, which occurs after the position shown in FIG. 3B, allows the sharp distal end of each of the needles 65a,b to protrude from the distal end opening of the needle guide tube 67a,b, and begin to enter the cannulated legs of the fastener (described later with reference to FIGS. 6A and 6B).

In FIG. 3C, the actuator 40 has moved distally bringing trigger 55 into contact with the timing engagement surface 180 of the timing lever 150. This movement of actuator 40 also moves needles 65a,b, which are mechanically fixed to the actuator 40, to fully insert the needles into the cannulated legs of the front-most fastener 50a (see FIG. 6B). The interference between trigger 55 and timing engagement surface 180, moves timing lever 150 downward, causing the retractor contours 165a,b of the timing legs 160a,b to move fastener support 270 rearward. As illustrated in FIG. 3C, movement of the fastener support 270 leaves the front-most fastener 50a without support, held only by the frictional contact with needles 65a,b.

In FIG. 3D, the actuator 40 has been pushed further downward, and contact surface 105 has pressed against push-pull tab 107, causing the guide tube support 73 to push the front-most fastener 50a from the magazine and deliver it to the tissue (see FIG. 12b of Danielson—US Patent application publication number 2009/0206127 A1). At the same time, cam track 61 (see FIG. 2B) has caused trigger 55 to lose contact with trigger engagement surface 180 of the timing lever. As the contact is lost timing lever 150 returns to its up position, forced by timing lever spring 155. This is the position shown in FIG. 3D. Once the timing lever 150 has returned, fastener support 270 is urged forward by fastener support spring 287 (see FIG. 5). However, the actual return of fastener support 270 to its initial forward position, is not possible until the needle guide tubes 67a,b move up out of the way. This happens when the user releases pressure on actuator thumb pad 43, and return spring 45 pulls the actuator 40 upward. When actuator 40 moves upwards, the needles retract inside the needle guide tubes 67a,b, and the proximal surface of detent receiver 93 engages push-pull tab 107, to pull guide tube support 73 and needle guide tubes 67a,b upward to the starting position shown in FIG. 3A.

Figure 4:
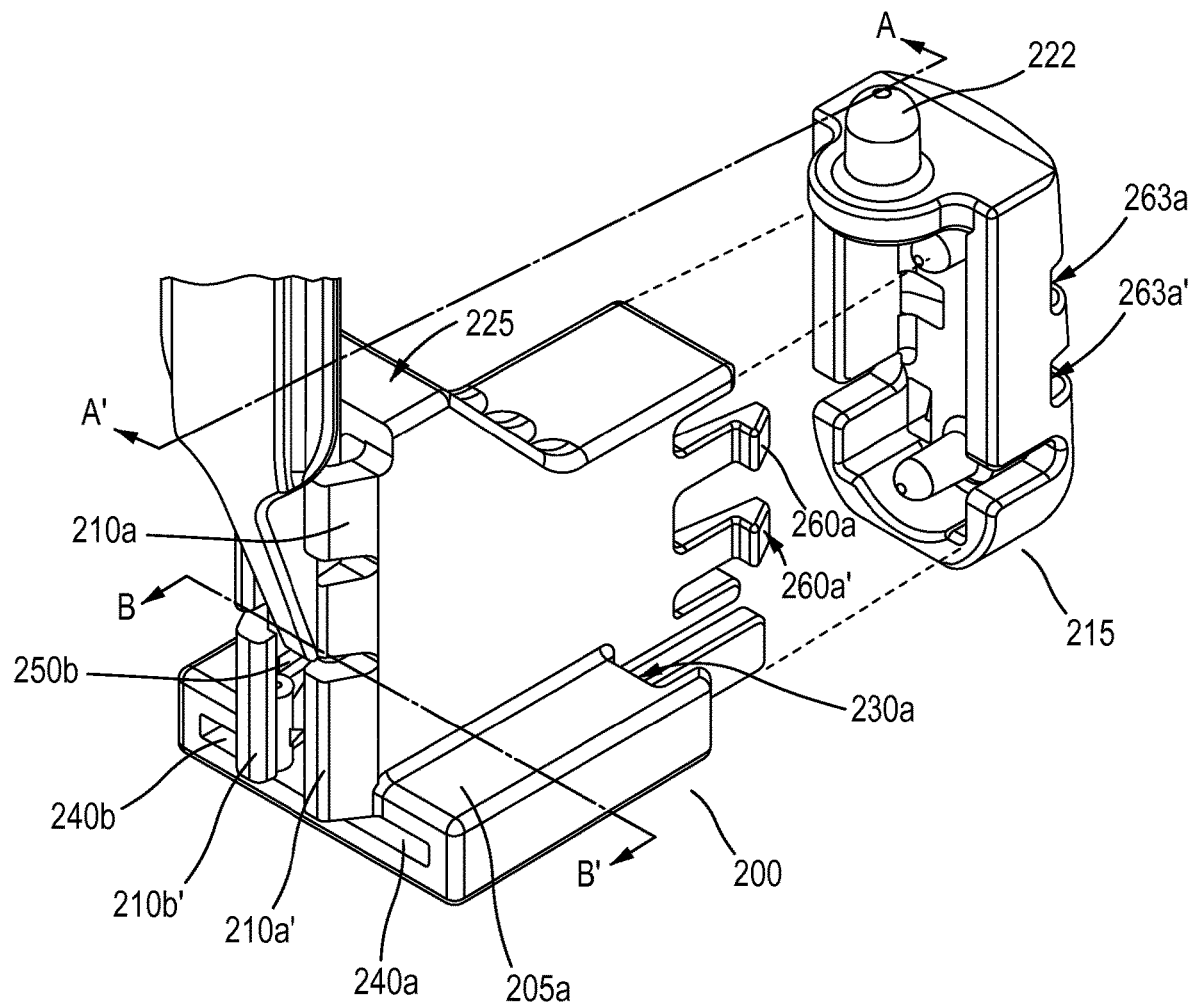
FIG. 4 shows a partially exploded perspective view of the magazine and cap and selected components normally assembled together.

FIG. 4 shows the magazine 200 removed from the apparatus and dis-assembled from cap 215. The cap 215 may be secured to the body of the magazine by various means known in the art such as adhesive bonding or ultrasonically welding. In one embodiment illustrated in FIG. 4, a releasable attachment is provided by cap latches 260a,a',b,b' on the magazine 200, which have a barbed shape at the end of a flexible arm. During assembly the flexible arms bend slightly to allow the cap latches 260a,a',b,b' to be inserted through openings in cap 215. Once fully inserted, the flexible arms straighten to their original shape, and the cap latches 260a,a',b,b' secure the cap by pressing against latch seats 263a,a',b,b' respectively. At the top of cap 215 there is a timing lever spring tab 222 which registers the distal end of the timing lever spring 155 to hold it in place.

Continuing with reference to FIG. 4, at the top of the magazine 200 there is a stop surface 225 which stops the distal motion of the actuator 40 by interfering with the actuator stop protrusion 120 (see FIG. 2A). Huggers 210a, a',b,b' extend from the front of the magazine 200 where they provide a sliding contact with the needle guide tubes 67a,b (see FIG. 7). The magazine 200 also has timing leg support surfaces 230a,b that provide surfaces along which the distal end of timing legs 160a,b (see FIG. 6A, 6B) may slide. This allows timing lever 150 to be only loosely guided in its motion by timing lever tab 175 (see FIG. 2b), which slides in timing lever slot 159 (see FIG. 2A). The critical reference geometry for timing lever 150 is provided by a sliding contact between timing legs 160a,b (see FIG. 2A) and timing leg support surfaces 230a,b.

Figure 5:
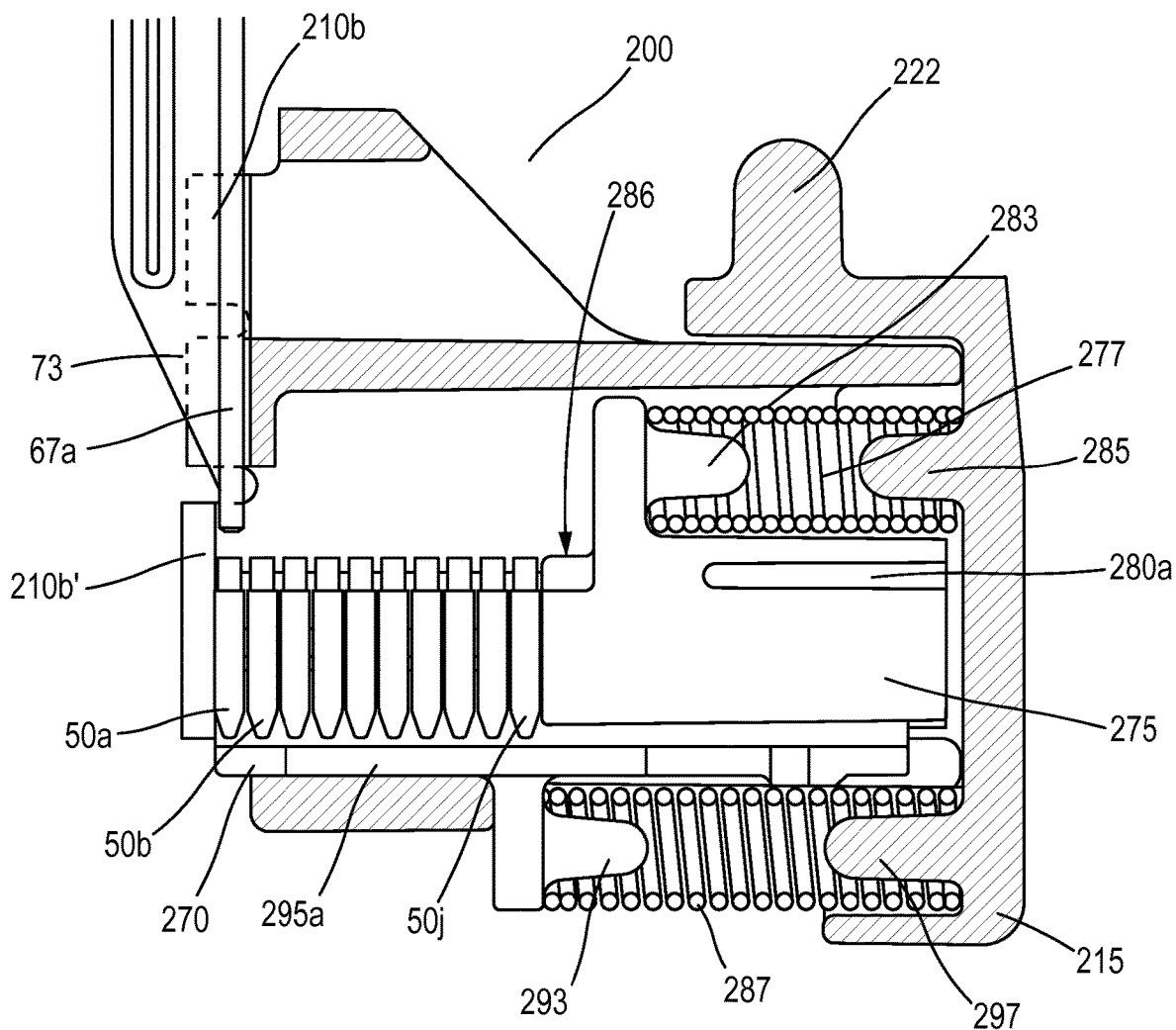
FIG. 5 shows a cross section of the magazine and cap taken along the A-A' plane of FIG. 4 and including non-sectioned views of some internal components.

FIG. 5 shows a cross section of the magazine 200 and cap 215 assembled together and taken along the A-A' plane of FIG. 4. The left side of FIG. 5, referred to as the front of magazine 200, shows the guide tube support 73 and needle guide tube 67a positioned against huggers 210b and 210b'. Within the magazine 200 are ten (10) fasteners 50a through 50j positioned on the fastener support 270. The front-most fastener 50a is in close contact with hugger 210b', and therefore positioned directly in alignment with needle guide tube 67a. Contact of the front-most fastener 50a with the huggers is assured due to contact with the remaining fasteners 50b-j which is urged forward by pusher 275 and pusher spring 277. In an exemplary embodiment, pusher 275 is fabricated by injection molding processes from a plastic material such as Nylon 66 (for example Zytel® 101L available from E.I. DuPont de Nemours & Co. of Wilmington, Del.) with smooth sliding surfaces facing the fastener support 270. Pusher spring 277 is a compression spring fabricated from, for example, Type-302 stainless steel. Pusher spring 277 is held in place by pusher spring tab 283, located on the pusher, and upper spring tab 285, located on the cap 215. Travel of the pusher 275 is guided by pusher tongues 280a,b which travel in pusher grooves 250a,b (see FIG. 4).

The exemplary embodiment of the present invention shown in FIG. 5 includes ten (10) fasteners 50a-j, but it will be understood by those skilled in the art that simple changes in dimensions of the components can be made to accommodate a smaller or larger number of fasteners in the assembly. A number of fasteners in the range of 1 to 25 is contemplated by the present invention in order to provide a sufficient number to close both short and long incisions.

Continuing with reference to FIG. 5, after one of the fasteners 50a-j is inserted into the tissue, the needle guide tubes move proximally to clear the way for fastener support 270 to move forward (returning to the position illustrated in in this FIG. 5 and in FIG. 3A). Once needle guide tubes 67a,b move proximally out of the way, pusher 275 is urged forward by pusher spring 277 to advance all remaining fasteners thereby bringing the next fastener (for example, 50b) into the front-most position.

When all fasteners have been deployed, a safety mechanism is introduced that prevents the needles 65a,b from being extended again. This is accomplished by pusher stop surface 286 which is the front-most portion of pusher 275. After the last fastener is delivered and the needle guide tubes 67a,b move up and out of the way, pusher 275 moves forward (left in FIG. 5) urged by pusher spring 277, to position pusher stop surface 286 directly below the needle guide tubes 67a,b. If the user presses on the actuator 40 in this condition the guide tubes are blocked from moving downward and the needles remain with the housing 25.

Continuing with reference to FIG. 5, the fasteners 50a-j are positioned on fastener support 270 which is urged toward the front of the magazine by fastener support spring 287. Fastener support 270 may be fabricated by injection molding processes using a material such as Food Grade Natural Acrylonitrile Butadiene Styrene ("ABS") (e.g. Lustran 433-000000 which is available from INEOS ABS Corporation of Addyston, Ohio). Fastener support spring 287 is a compression spring fabricated from, for example, Type-302 stainless steel. It is held in place by fastener support spring tab 293, located on the fastener support 270, and lower spring tab 297, located on the cap 215. Travel of the fastener support is guided by fastener support tongues 295a,b which travel in fastener support grooves 240a,b (see FIG. 4). As will be described below, the travel of the fastener support 270 reciprocates (left and right in FIG. 5) over a very short distance. In an alternate embodiment, the fastener support spring 287 could be replaced by a simple resilient arm. In such an embodiment, the resilient arm, having an effective spring rate of approximately 1 lb/inch, is molded as part of one of the contacting parts, the magazine 200, the fastener support 270 or the cap 215, to provide the necessary restoring force to move the fastener support 270.

FIGS. 6A and 6B show the fastener support 270 together with the front-most fastener 50a, guide tube support 73, needle guide tubes 67a,b and the distal portion of timing legs 160a,b, to illustrate detailed features of these parts. The fastener 50a is the type of fastener described by Danielson (US patent application publication number 2009/0206127 A1) and made from bioabsorbable materials. It is shown having a bridge 313 connecting two cannulated legs 317a and 317b each with barbs 333a and 333b respectively. The cannulated legs 317a,b have openings 325a,b that are chamfered at the top of legs 317a,b. The chamfer provides a slightly larger diameter for openings 325a,b to facilitate insertion of needles 65a,b respectively. The fastener support 270 has a ridge 340 on which the bridge 313 of the fastener rests. Below the ridge 340, the cross-sectional shape of the fastener support 270 is designed to match features of the fasteners. In particular, sidebars 305a,b run the full length of the fastener support 270 and are shaped to restrain the barbs 333a,b of the fasteners from being easily dislodged upward. Thus the fasteners are able to slide in a linear fashion along the length of ridge 340 of the fastener support 270 arriving at the front-most position with a predictable position as illustrated.

Continuing with reference to FIG. 6A, the fastener support tongues 295a,b are interrupted at the rear by notches 345a,b which engage timing lever legs 160a,b. The front-most fastener 50a is positioned directly below the needle guide tubes 67a,b and aligned with the needles 65a,b (retracted within the tubes) because both are in slidable contact with the huggers 210a,a',b,b' (see FIG. 5). Timing leg 160a is shown with the distal end positioned in notch 345a of the fastener support. The rearward edge of notch 345a is in direct contact with retractor contour 165a due to the urging of fastener support spring 287 (see FIG. 5).

In FIG. 6B the same components as illustrated in FIG. 6A are shown in a position previously described with reference to FIG. 3C. Downward movement "A" advances the needles 65a,b inserting them into the cannulated legs 317a,b of the front-most fastener 50a. Simultaneously the downward movement "B" of timing legs 160a,b causes retractor contours 165a,b to press against notches 345a,b to move the fastener support 270, as illustrated by arrow "C", away from the front-most fastener 50a. This action, taken immediately after the needles 65a,b are inserted into the fastener, leaves front-most fastener 50a without support from the fastener support 270. Without support from the fastener support 270, the front-most fastener 50a is supported only by frictional contact with needles 65a,b, and can be pushed by needle guide tubes 67a,b to move distally out of the magazine 200.

Needles 65a,b are made from surgical grade stainless steel or other similarly strong material(s) and sharpened with a conical point by means familiar to those in the art. The needle guide tubes 67a,b are made from stainless steel and have an external surface that is similar in shape and size to the external surface of the fastener legs 317a,b. Other material(s) can be used to make the needle guide tubes 67a,b. In a preferred embodiment, the needle guide tubes 67a,b and fastener legs 317a,b are cylindrical in shape and have the same outside diameter. The needle guide tubes 67a,b are spaced apart by a distance equal to the distance separating fastener legs 317a and 317b from one another. The needle guide tubes 67a,b are rigidly fixed to the guide tube support 73 by means known in the art. In one embodiment, the guide tube support 73 is made by injection molding using a material such as Acrylonitrile Butadiene Styrene (ABS) or acrylics (for example, Cyrolite® acrylic based compounds available from Cryo Industries, Rockaway, N.J.). The needle guide tubes 67a,b may be separately fabricated with a spacer-attachment structure to hold them parallel to each other. The needle guide tubes 67a,b with such an attachment structure may be attached to guide tube support 73 by means know in the art such as screws, thermo-staking, or adhesive bonding. The stainless steel needle guide tubes 67a,b may also be insert molded to be part of guide tube support 73 as a molded part.

Figure 7:
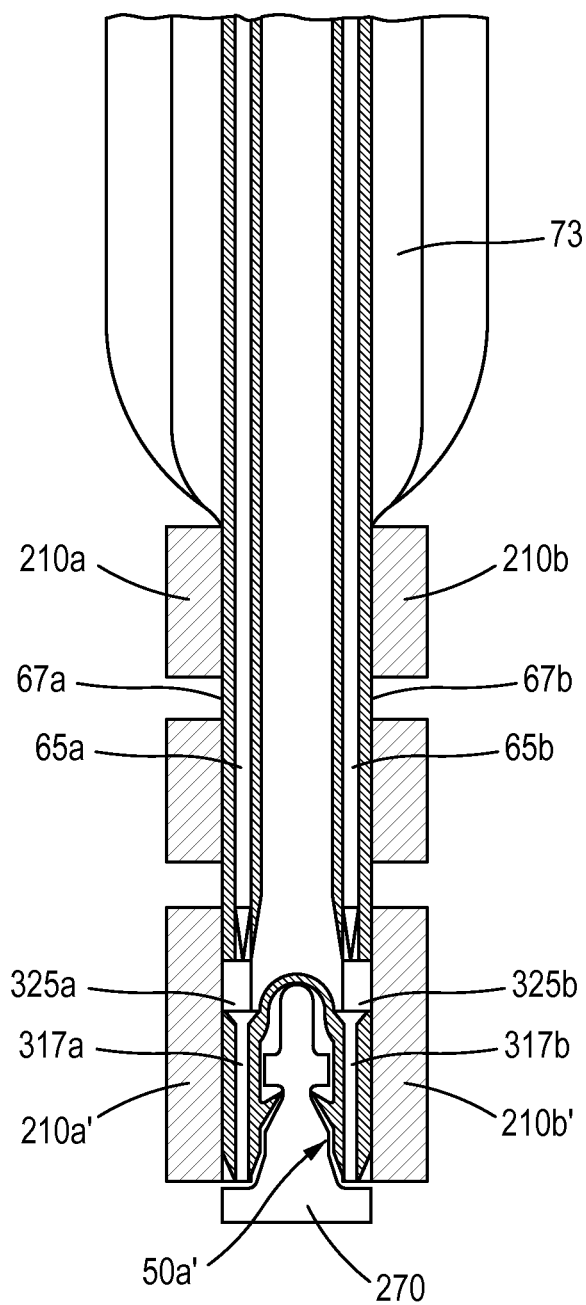
FIG. 7 shows a cross section of the components of FIG. 4 taken along the B-B' plane, positioned at the start of delivery of a fastener as shown in FIG. 6A.

FIG. 7 shows a cross section of the components of FIG. 4 taken along the B-B' plane with the selected components positioned as previously illustrated in FIGS. 3A and 6A. The front-most fastener 50a is shown positioned on fastener support 270 directly below the needle guide tubes 67a,b. The legs 317a and 317b of the front-most fastener 50a are in slidable contact with the huggers 210a' and 210b' respectively. Similarly the needle guide tubes 67a,b are in slidable contact with huggers 210a,a',b,b'. The needles 65a,b are constrained to move within the needle guide tubes 67a,b which causes them to be axially aligned with openings 325a,b. By the sequence described with reference to FIGS. 3A-3D, the needle guide tubes 67a,b move downward to contact the top of legs 317a,b and then the needles 65a,b advance from within the needle guide tubes to enter openings 325a,b.

FIG. 7 illustrates the most demanding functionality of the present invention; that is, introducing the distal points of needles 65a,b into the openings 325a,b at the top of the fastener legs 317a,b respectively. This is accomplished without impossibly tight manufacturing processes by registering the critical parts and placing them into sliding contact with one another. This contact is created by the features on the magazine 200 called huggers 210a,a',b,b'. By adapting the needle guide tubes 67a,b and fastener legs 317a,b to have the same shape (e.g. cylindrical) and to have the same cross-sectional dimensions (e.g. outside diameter), both parts can be urged into contact with a common surface. In one embodiment, illustrated in FIG. 7, huggers 210a,a',b,b' are in sliding contact with needle guide tubes 67a,b and front-most fastener 50a, which places the needles 65a,b in axial alignment with the openings 325a,b. Because the magazine 200 is free to move within the magazine slots 207a,b (see FIG. 2B) it is able to remain referenced to the needle guide tubes 67a,b due to the sliding contact of the huggers 210a,a',b,b'.

The apparatus of the present invention has been described with reference to ten (10) bioabsorbable fasteners of the type described by Danielson (US patent application publication number 2009/0206127 A1). Those skilled in the art will realize that the benefits of the invention may be applied to other fasteners, whether made from bioabsorbable materials or not. Realizing that the objective is to deliver fasteners one at a time from a cartridge having a multiplicity of fasteners, it will be apparent that the apparatus may be adapted by obvious modifications to deliver fasteners in greater or lesser number than ten. Alternate embodiments also can work with fasteners having a greater or lesser number of legs than two. Fasteners that do not have cannulated legs can benefit from the present invention if such fasteners are adapted to have features such as holes or slots into which guiding elements, for example needles, may be inserted. While the present invention has been set forth in terms of a specific embodiment or embodiments, it will be understood that the present invention herein disclosed may be modified or altered to other configurations. Accordingly, the invention is not limited only to disclosed details.

The invention claimed is:

1. Apparatus for closing two sides of an incision or cut in skin tissue, the apparatus comprising:
   a housing having a proximal end and a distal end, the housing adapted to be held in the hand of a user;
   an actuator configured to be moved into the housing by the user of the apparatus along a first axis that extends from the proximal end of the housing to the distal end of the housing along a length of the actuator;
   a plurality of fasteners positioned within the housing;
   a pusher in contact with the plurality of fasteners and configured to urge the plurality of fasteners along a second axis which is orthogonal to the first axis; and
   at least one needle connected to the actuator and adapted to releasably engage one of the plurality of fasteners at a time and to move along the first axis to exit the distal end of the housing to deliver the fastener into each of the two sides of the incision or cut.

2. The apparatus of claim 1 further comprising a locking mechanism that prevents the fastener from exiting the distal end of the housing prior to user manipulation of the locking mechanism.

3. The apparatus of claim 1 further comprising a safety mechanism that prevents the at least one needle from being exposed out of the distal end of the housing after all of the plurality of the fasteners have exited the distal end of the housing.

4. The apparatus of claim 1 wherein each of the plurality of fasteners is bioabsorbable.

5. Apparatus for closing two sides of an incision or cut in skin tissue, the apparatus comprising:
   a housing having a proximal end and a distal end, the housing adapted to be held in the hand of a user;
   an actuator having a first position extending from the proximal end of the housing and configured to be moved into the housing to a second position by the user of the apparatus along a length of the actuator;
   a plurality of fasteners positioned within the housing such that one of the fasteners at a time is delivered by the apparatus when the actuator is moved by the user from the first position to the second position; and
   an insertion device connected to the actuator and adapted to hold by frictional contact one of the fasteners at a time, the insertion device having sharp distal ends which extend distally beyond the fastener as the actuator moves from the first position to the second position to deliver the fastener, a portion of the fastener thus being inserted into each of the two sides of the incision or cut.

6. The apparatus of claim 5 further comprising a spring operatively connected to the actuator and configured to be deformed when the user moves the actuator from the first position to the second position and to provide a restoring force to return the actuator to the first position.

7. The apparatus of claim 5 wherein each of the plurality of fasteners is bioabsorbable.

8. The apparatus of claim 5 further comprising a locking mechanism that prevents the fastener from exiting the distal end of the housing prior to user manipulation of the locking mechanism.

9. The apparatus of claim 5 further comprising a safety mechanism that prevents the insertion device from being exposed out of the distal end of the housing after all of the plurality of the fasteners have exited the distal end of the housing.

10. Apparatus for closing two sides of an incision or cut in skin tissue, the apparatus comprising:
   a housing adapted to be held in the hand of a user;
   an actuator configured to be moved by the user linearly along a length of the actuator, into the housing, and at a speed controlled by the user;
   a plurality of fasteners disposed within the housing; and
   at least one needle rigidly attached to the actuator and adapted to hold by frictional contact one of the plurality of fasteners at a time and to exit the housing to deliver the fastener when the user moves the actuator such that a portion of the fastener is inserted into each of the two sides of the incision or cut.

11. The apparatus of claim 10 wherein the actuator comprises a thumb pad located at a proximal end of the actuator, movement of the actuator into the housing results when pressure is applied to the thumb pad by a thumb of the user.

12. The apparatus of claim 11 further comprising a spring operatively connected to the actuator and configured to be deformed when the user moves the actuator into the housing and to provide a restoring force to return the actuator to a starting position when the user releases pressure on the thumb pad.

13. The apparatus of claim 10 further comprising a locking mechanism that prevents the fastener from exiting a distal end of the housing prior to user manipulation of the locking mechanism.

14. The apparatus of claim 10 further comprising a safety mechanism that prevents the at least one needle from being exposed out of a distal end of the housing after all of the plurality of fasteners have exited the distal end of the housing.

15. The apparatus of claim 10 wherein each of the plurality of fasteners is bioabsorbable.

16. The apparatus of claim 15 wherein each of the bioabsorbable fasteners comprises a first leg and a second leg configured such that the first leg is a portion of the fastener inserted into one of the two sides of the incision or cut and the second leg is another portion of the fastener inserted into the other side of the incision or cut.

* * * * *